United States Patent [19]

Faccini

[11] Patent Number: 4,805,241
[45] Date of Patent: Feb. 21, 1989

[54] THERAPEUTIC GARMENT FOR A CHRONIC CLOTHES RIPPING PATIENT

[76] Inventor: Lino A. Faccini, 1998 37B Rte. 112, Coram, N.Y. 11727

[21] Appl. No.: 117,978

[22] Filed: Nov. 9, 1987

[51] Int. Cl.[4] .......................... A41D 1/00; A41D 1/04
[52] U.S. Cl. ............................................ 2/102; 2/119
[58] Field of Search ................. 2/102, 69, 75, 49 R, 2/80, 94, 96

[56] References Cited

U.S. PATENT DOCUMENTS

| | | | |
|---|---|---|---|
| 3,724,101 | 4/1973 | Slezak | 2/69 X |
| 3,997,982 | 12/1976 | Holland | 2/102 X |
| 4,382,302 | 5/1983 | Watson | 2/102 |
| 4,658,442 | 4/1987 | Tomlinson et al. | 2/102 X |
| 4,710,979 | 12/1987 | Bull et al. | 2/49 R X |
| 4,723,323 | 2/1988 | Wright | 2/49 R |

Primary Examiner—Werner H. Schroeder
Assistant Examiner—Jeanette E. Chapman
Attorney, Agent, or Firm—Michael I. Kroll

[57] ABSTRACT

A therapeutic garment is provided for a chronic clothes ripping patient which consists of a vest and a pair of short leg extensions worn by the patient that includes a plurality of patches that can be peeled away by the patient and a plurality of puller threads that can be also pulled away by the patient when so desired.

12 Claims, 1 Drawing Sheet

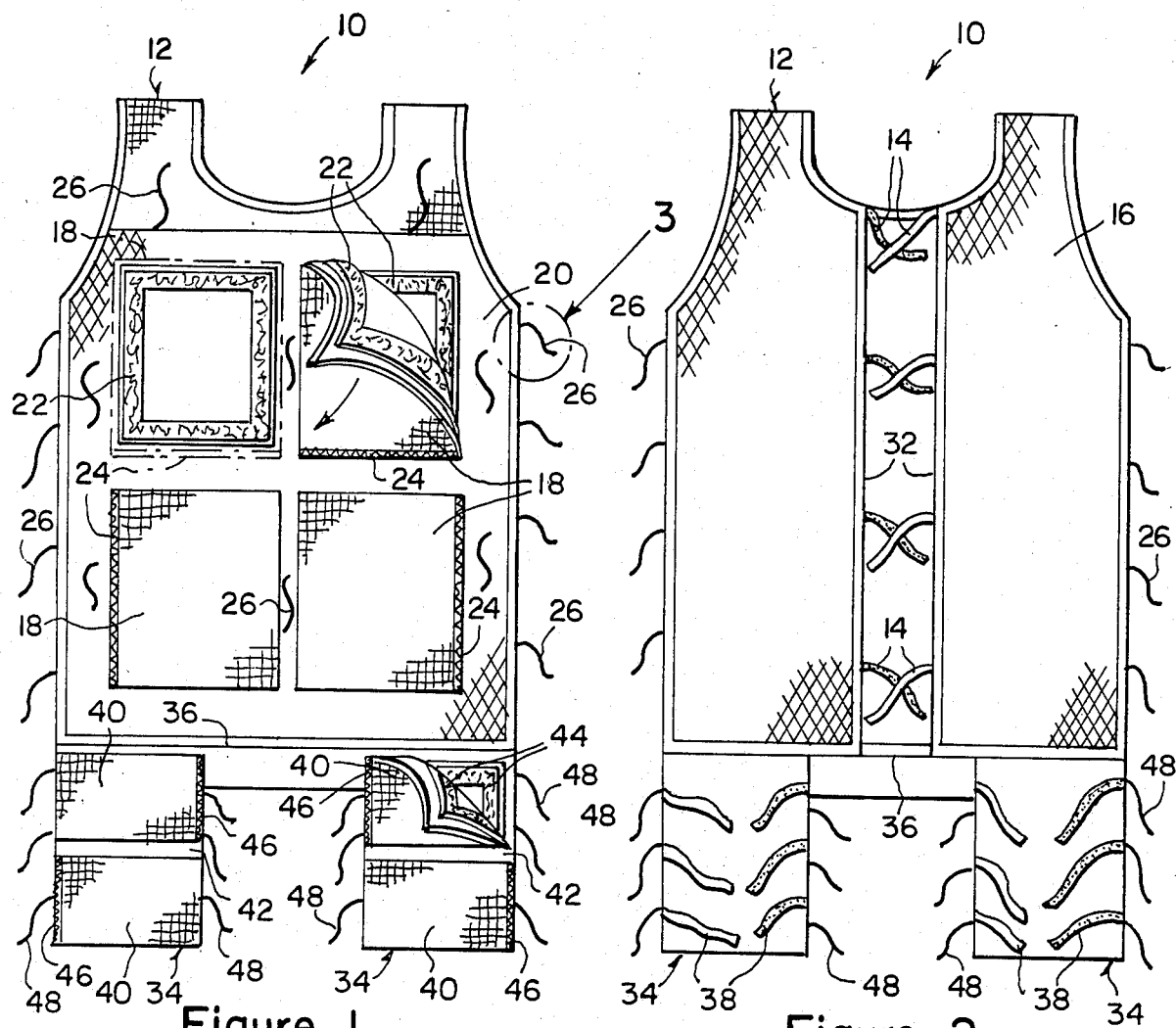
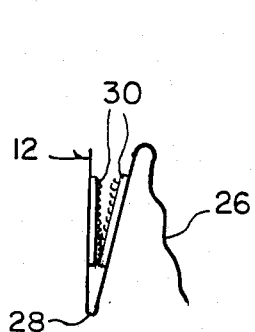
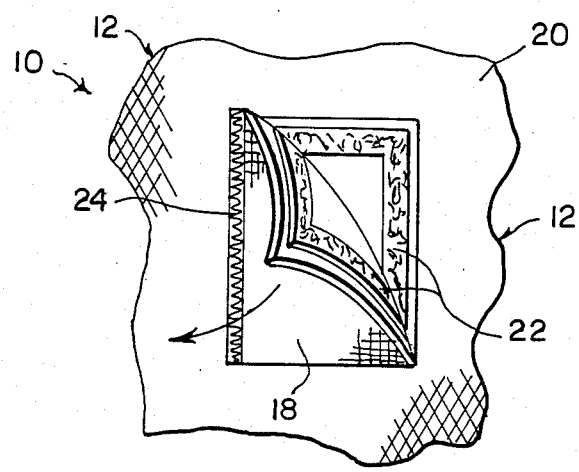

THERAPEUTIC GARMENT FOR A CHRONIC CLOTHES RIPPING PATIENT

BACKGROUND OF THE INVENTION

1. Field of the Invention

The instant invention relates generally to disposable wearing apparel and more specifically it relates to a therapeutic garment for a chronic clothes riping patient.

2. Description of the Prior Art

Currently in Developmental Centers, many patients destroy their clothing either through tearing or unraveling. The only consistently implemented procedure is having the patient wear jumpsuits which they do shread and tear. Therefore this behavior remains untreated and costly to the state centers.

Numerous disposable wearing apparel have been provided in prior art that are adapted to be worn by patients and then discarded after use. While these units may be suitable for the particular purpose to which they address, they would not be as suitable for the purposes of the present invention as heretofore described.

SUMMARY OF THE INVENTION

The invention consists of a therapeutic garment to be used with a developmentally disabled patient who tears and/or unravels clothing. The therapeutic garment would make proven effective procedures of positive and negative practice more efficiently implementable. Since the therapeutic garment will make both positive and negative practice more easily implementable, it should be effective in dealing with the above maladaptive behaviors.

Negative Practice is defined as the repetition or performance of a certain behavior in order to decrease or eliminate that behavior. This is usually due to the fatigue that sets in and over time becomes associated with the performance of the behavior. As a result, the termination of the behavior becomes associated with the dissipation of fatigue and reinforces not to perform the behavior.

Positive Practice is the repetition of an act or behavior that is appropriate in a situation which a patient normally misbehaves.

A primary object of the present invention is to provide a therapeutic garment for a chronic clothes ripping patient that will overcome the shortcomings of the prior art devices.

Another object is to provide a therapeutic garment for a chronic clothes ripping patient that allows for either positive or negative practice for upper or lower body garments as well as for thread unravelers.

An additional object is to provide a therapeutic garment for a chronic clothes ripping patient that can be transported easily to different environments instead of accumulating rags and good clothes for the patient.

A further object is to provide a therapeutic garment for a chronic clothes ripping patient that can be implemented quickly even with a resistive patient.

A still further object is to provide a therapeutic garment for a chronic clothes ripping patient that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a front view of the invention.

FIG. 2 is a rear view of the invention.

FIG. 3 is a detail view as indicated by arrow 3 in FIG. 1 showing one typical puller thread assembly.

FIG. 4 is an enlarged front view with parts broken away of one of the vest patches in greater detail.

DETAILED DESCRIPTION OF THE PREFERRED EMBODIMENTS

Turning now descriptively to the drawings, in which similar reference characters denote similar elements throughout the several views, FIGS. 1 and 2 illustrate a therapeutic garment 10 for a chronic clothes ripping patient (not shown) in which the therapeutic garment 10 consists of a vest 12 to be worn over torso of the patient, fasteners 14 for removably securing the vest 12 to the torso of the patient from the rear 16 of the vest 12, a plurality of vest patches 18 to be carried on front 20 of the vest 12 and fasteners 22 for removably attaching each of the vest patches 18 to the front 20 of the vest 12 so the each of the vest patches 18 can be peeled away by the patient when so desired.

Each of the vest patches 18 is permanently attached at one edge, by sewing, (see FIG. 4) to the front 20 of the vest 12 forming a hinge 24 so as to prevent loss once each of the best patches 18 is peeled away.

A plurality of vest puller threads 26 are each removably separable and affixed at one end 28 to the vest 12 to prevent detachment therefrom so that each of the vest puller threads 26 can be pulled away by the patient when so desired. As best seen in FIG. 3, each of the vest puller threads 26 is removably separable to the vest 12 by hook and loop fastener tabs 30.

Fasteners 14 include a plurality of hook and loop fabric fastener straps attached to opposite sides of a rear placket 32 in the vest 12 which will mate and engage with each other, while fasteners 22 are hook and loop fastener elements.

The therapeutic garment 10 further contains a pair of short leg extensions 34 attached to waist 36 of the vest 12 to be worn over each thigh of the patient. Fasteners 38, identical in construction to fasteners 14, are for removably securing each of the short leg extensions to each thigh of the patient from the rear of each of the short leg extensions 34. A plurality of leg patches 40 identical in construction to vest patches 18, are carried on front 42 of each of the short leg extensions 34. Fasteners 44, identical in construction to fasteners 22 removably attached each of the leg patches 40 to the front 42 of each of the short leg extensions 34 so that each of the leg patches 40 can also be peeled away by the patient when so desired and held by a hinge 46. Leg puller threads 48, identical in construction to vest puller threads 26 are also provided so that each of the leg puller threads can be pulled away by the patient when so desired.

The therapeutic garment 10 can be used in the negative practice in which the patient wants to tear and rip their shirt and pants. The patient wearing the therapeutic garment 10 prompted by a therapist, peels and replaces the vest and leg patches 18 and 40 while at the same time pulls and sets the vest and leg puller threads 26 and 48 during a predetermined time interval until this desire by the patient to do so stops.

The therapeutic garment 10 can be used in the positive practice in which the patient wants to undress. The patient wearing the therapeutic garment 10 prompted by a therapist, can open and close the fasteners 14 and 38 on the vest 12 and short leg extensions 34 to undress and dress during a predetermined time interval until this desire by the patient to do so stops.

The hinges 24 designated for vest patches 18 and the hinges 46 designated for leg patches 40 as shown in FIG. 1 are illustrative only and that the placement of the hinges 24 and 46 are dependent on assessment information for each patient.

It will be understood that each of the elements described above, or two or more together, may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

1. A therapeutic garment for a chronic clothes ripping patient which comprises:
   (a) a vest to be worn over torso of the patient;
   (b) means for removably securing said vest to the torso of the patient from the rear of said vest;
   (c) a plurality of vest patches to be carried on front of said vest, each of said vest patches being permanently attached at one edge to the front of said vest forming a hinge so as to prevent loss once each of said vest patches is peeled away; and
   (d) a plurality of vest puller threads each removably separable and affixed at one end to said vest to prevent detachment therefrom so that each of said vest puller threads can be pulled away by the patient when so desired.

2. A therapeutic garment as recited in claim 1, wherein said removably securing means for said vest includes:
   (a) said vest having a rear placket;
   (b) a plurality of hook fabric fastener straps attached to one side of said rear placket; and
   (c) a plurality of matching loop fabric fastener straps attached to other side of said rear placket, each of which mates and engages with one of said hook fabric fastener straps.

3. A therapeutic garment as recited in claim 2, wherein said removably attaching means for each of said vest patches includes a hook and loop fastener elements.

4. A therapeutic garment as recited in claim 3, wherein each of said vest puller threads is removably separable to said vest by hook and loop fastener tabs.

5. A therapeutic garment as recited in claim 4, wherein each of said vest patches is permanently attached at one edge to the front of said vest by sewing the one edge of said vest patch to said vest.

6. A therapeutic garment as recited in claim 5, further comprising:
   (a) a pair of short leg extensions attached to waist of said vest to be worn over each thigh of the patient;
   (b) means for removably securing each of said short leg extensions to each thigh of the patient from the rear of each of said short leg extensions;
   (c) a plurality of leg patches to be carried on front of each of said short leg extensions; and
   (d) means for removably attaching each of said leg patches to the front of each of said short leg extensions so that each of said leg patches can be peeled away by the patient when so desired.

7. A therapeutic garment as recited in claim 6, wherein each of said leg patches is permanently attached at one edge to the front of each of said short leg extensions forming a hinge so as to prevent loss once each of said leg patches is peeled away.

8. A therapeutic garment as recited in claim 6, further comprising a plurality of leg puller threads, each removably separable and affixed at one end to each of said short leg extensions to prevent detachment therefrom so that each of said leg puller threads can be pulled away by the patient when so desired.

9. A therapeutic garment as recited in claim 8, wherein said removably securing means for each of said short leg extensions includes:
   (a) a plurality of hook fabric fastener straps attached to one side of said short leg extension; and
   (b) a plurality of matching loop fabric fastener straps attached to other side of said short leg extension, each of which mates and engages with one of said hook fabric fastener straps.

10. A therapeutic garment as recited in claim 9, wherein said removably attaching means for each of said leg patches includes a hook and loop fastener elements.

11. A therapeutic garment as recited in claim 10, wherein each of said leg puller threads is removably separable to each of said short leg extensions by hook and loop fastener tabs.

12. A therapeutic garment as recited in claim 11, wherein each of said leg patches is permanently attached at one edge to the front of each of said short leg extensions by sewing the one edge of said leg patch to said short leg extension.

* * * * *